United States Patent [19]

Ogle

[11] 4,253,501

[45] Mar. 3, 1981

[54] TRANSFER SYSTEM

[75] Inventor: Robert W. Ogle, Newport Beach, Calif.

[73] Assignee: IMS Limited, So. El Monte, Calif.

[21] Appl. No.: 92,678

[22] Filed: Nov. 9, 1979

[51] Int. Cl.³ .............................................. B65B 3/02
[52] U.S. Cl. .................................... 141/27; 141/286; 141/330; 128/214 F; 128/DIG. 12; 137/43; 210/136
[58] Field of Search ..................... 141/19, 2, 329, 330, 141/54–59, 290–310, 382–389, 392, 285, 286, 18–27; 128/214 R, 214 F, DIG. 12; 210/136; 137/43

[56] References Cited

U.S. PATENT DOCUMENTS

| | | | |
|---|---|---|---|
| 2,738,796 | 3/1956 | Chadwick | 137/43 |
| 4,030,495 | 6/1977 | Virag | 128/214 F |
| 4,063,553 | 12/1977 | Karsh | 128/214 F |
| 4,189,385 | 2/1980 | Greenspan | 210/136 |

Primary Examiner—Houston S. Bell, Jr.
Attorney, Agent, or Firm—Joseph E. Mueth

[57] ABSTRACT

A transfer device for withdrawal of aliquots from a container of bulk solution is provided with a body having a tapered chamber, a first passage venting the smaller end of the chamber to the surrounding air, a second passage communicating at one end with the larger end of the chamber, and a third passage having one end for withdrawal of fluid therefrom. A tapered valve element is received within the chamber for movement between first and second conditions in response to changes in the presence differential between the first and second passages. The first condition provides a fluid seal between the first and second passages by engagement of the valve element with the walls of the chamber for pressures within the second passage greater than that within the first passage, and the second condition provides a fluid path from the first passage to the second passage for pressures within the second passage somewhat less than that within the first passage. The device further includes structure placing the other ends of the second and third passages in commuication with the interior of the container of bulk solution, such that a path is provided for air to be drawn into the container when aliquots of solution are withdrawn from the container through the third passage.

17 Claims, 5 Drawing Figures

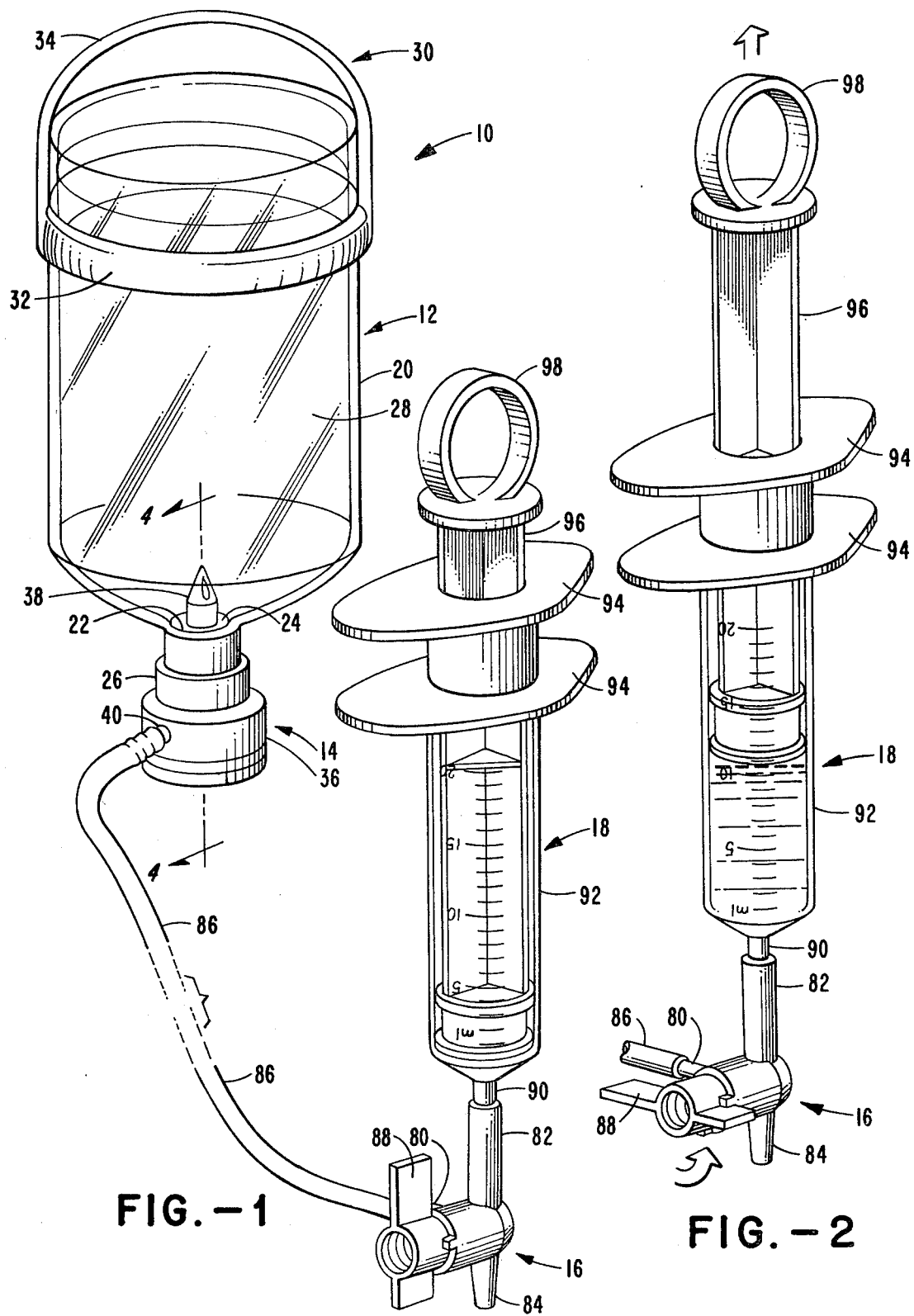

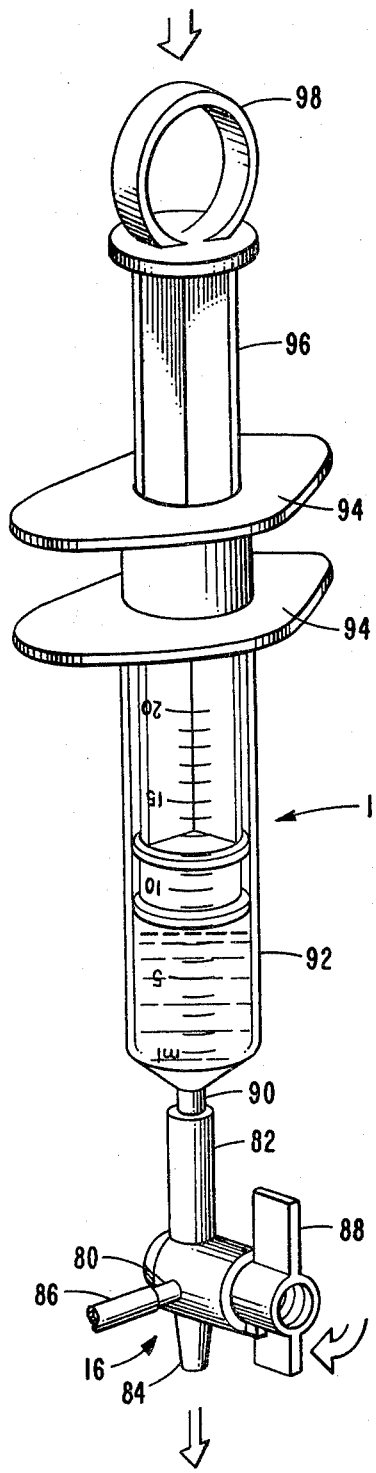
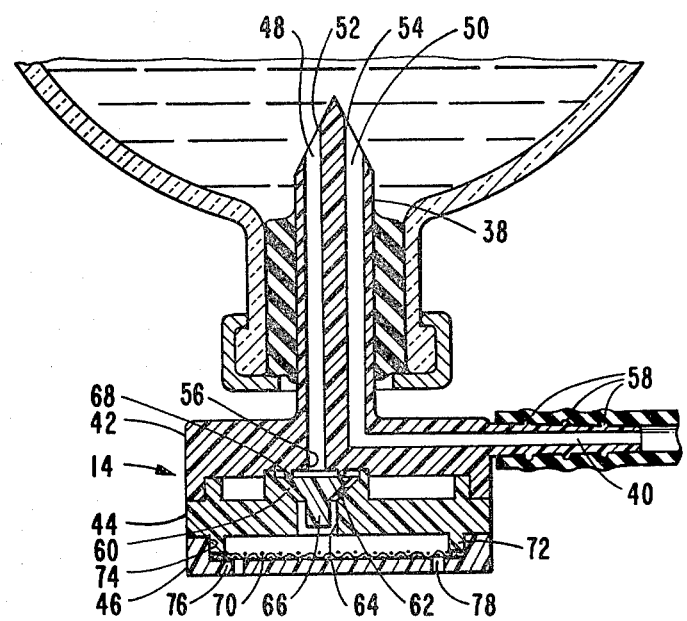
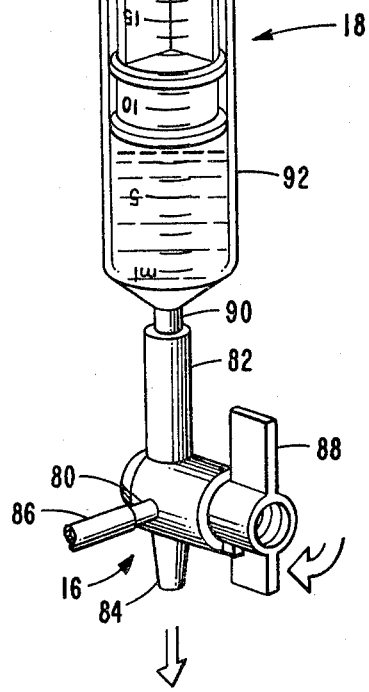
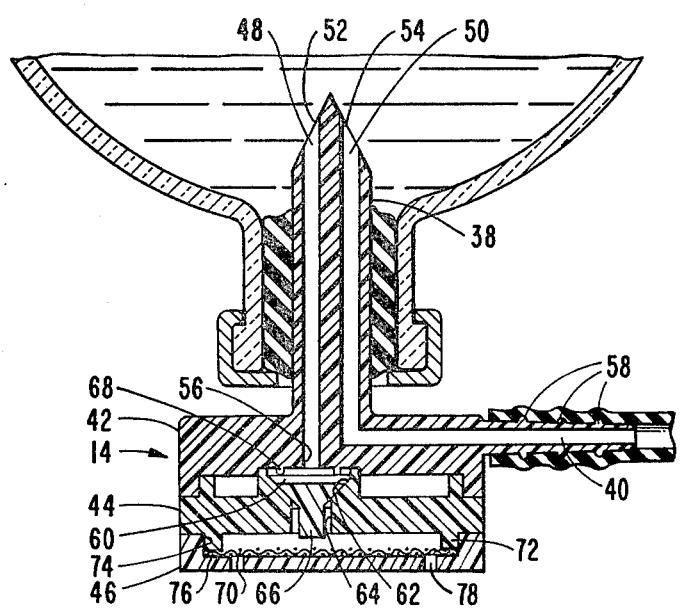

TRANSFER SYSTEM

BACKGROUND OF THE INVENTION

1. Field of the Invention

This invention relates to the fluid transfer art and more particularly to an improved system for transferring aliquots of a sterile solution from a bulk container to a plurality of other containers.

2. Description of the Prior Art

There have heretofore been proposed several types of devices for withdrawing aliquots from a container of bulk solution. The most common such device includes a conventional syringe for withdrawing aliquots of sterile solution from a stoppered bottle. In such cases, a volume of air is commonly injected into the bottle with the syringe to facilitate withdrawal of the desired aliquot of solution. If no air is injected, a partial vacuum develops within the bottle, making withdrawal of solution therefrom very difficult. However, the introduction of non-sterile air to the bottle may contaminate the solution contained therein and lead to serious medical consequences to a patient receiving the solution.

The problems associated with the withdrawal of liquid from a container of sterile solution are most severe when relatively large quantities of liquid are to be withdrawn on a frequent basis. Such is the case, for example, when hospital pharmacies add aliquots of concentrated aminophylline, KCl or multiple vitamin injection (MVI) to containers of intravenous solution. The concentrated additives are provided in bulk containers from which the desired aliquots must be taken, and the process of transferring aliquots from the bulk containers to different bottles of IV solution is repeated numerous times each day. It is thus of extreme importance in such cases that each transfer be effected with as little contamination as possible of the solution within the bulk container.

Devices have been proposed for venting the interior of a bottle from which quantities of solution are to be removed to allow air to be drawn into the bottle and thus equalize the pressures within and without the bottle. A filter may then be provided for removing unwanted impurities from the air drawn into the bottle. The prior vent structures have generally involved a passage open to the outside air and leading to the interior of the bottle, closed only by a filter element such as a small wad of cotton. Such devices, however, are subject to leakage through the filter element when the bottle is turned upside down for removal of solution therefrom. The problem of leakage is particularly acute where it is desired to hang the bottle upside down for long periods of time to remove successive aliquots therefrom.

Therefore, in many applications it is desirable to provide a vented device for aseptic transfer of aliquots from a container of bulk solution without leaking or spilling any of the solution, regardless of the orientation of the container.

SUMMARY OF THE INVENTION

Briefly, the present invention comprises a transfer device for the withdrawal of aliquots from a container of bulk solution having body means with first walls defining a tapered chamber, second walls defining a first passage venting the smaller end of the chamber to the surrounding air, third walls defining a second passage communicating at one end with the larger end of the chamber and fourth walls defining a third passage having one end for withdrawal of fluid therefrom, the third passage being free of communication with the first and second passages and the second chamber within the body means; a tapered valve element received within the chamber for movement between first and second conditions in response to changes in pressure differential between the first and second passages, the first condition providing a fluid seal between the first and second passages by engagement of the valve element with the first walls of the chamber for pressures within the second chamber greater than that in the first passage, and the second condition providing a fluid path from the first passage to the second passage for pressures within the second passage somewhat less than that within the first passage; and means for placing the other ends of the second and third passages in communication with the interior of the container of bulk solution; whereby a path is provided for air to be drawn into the container through the first and second passages when aliquots are withdrawn from the container through the third passage, but fluid is not able to escape from the container through the first and second passages.

The valve element may be resilient and may comprise a a conical member having a coaxial cylindrical portion depending from its apex. The tapered chamber may then comprise a conical cavity having a coaxial cylindrical cavity depending from its apex, the first passage communicating with the chamber through the cylindrical cavity. The valve element is somewhat smaller than the chamber for movement therein between the first and second condition. The means for placing the other ends of the second and third passages in communication with the interior of the container may comprise stopper piercing means projecting from the body means and having a sharpened outer end. The stopper piercing means may have a pair of passages extending from the other ends of the second and third passages, respectively, to corresponding openings adjacent the sharpened outer end.

The device may be part of a system for the dispensation of aliquots of a bulk solution which also includes a container of bulk solution and flow valve means for regulating the flow of fluid from the container through the third passage. The system may further include a syringe for withdrawing aliquots of the solution from the container through the third passage and flow valve means.

It is an object of the present invention to provide a device for aseptically withdrawing aliquots from a container of bulk solution.

It is another object of the present invention to provide a device for the aseptic transfer of aliquots from a container of bulk solution over a substantial period of time without spillage or leakage.

It is a further object of the present invention to provide a device for simply and easily transferring aliquots from a container of bulk solution without contaminating the solution.

It is a still further object of the present invention to provide a simple and disposable system for the dispensation of aliquots of a sterile solution.

The device of the present invention includes an air vent which is both filtered and valved to prevent the introduction of impurities into the container of bulk solution and to prevent the leakage of solution therefrom. The withdrawal of solution through a separate passage to the interior of the container results in the passage of air through the valve and into the container. The tapered valve element acts as a poppet valve for axial movement between open and closed conditions relative to the tapered seat formed by the interior of the valve chamber in response to variations in the pressure differential between the inlet and the outlet of the valve. The withdrawal of fluid from the interior of the container causes the pressures within the container to decrease, eventually resulting in a pressure at the outlet to the valve chamber which is somewhat less than that at the inlet to the valve chamber. At this point, the valve element opens to allow passage of air to the interior of the container. The partial vacuum within the container will thus be relieved, causing the pressure at the outlet to the valve chamber to again close the valve. In this way, filtered air is admitted into the container upon withdrawal of solution therefrom, however, the valve entirely prevents leakage of solution in the reverse direction through the air way.

In the case of the dispensation of a plurality of aliquots over an extended period of time, the container of bulk solution may be oriented upside down to enhance the withdrawal of fluid therefrom without causing any leakage. The container may be hung in this position until its entire contents have been removed, greatly reducing the manual manipulation required of the pharmacist over the course of the day. The entire operation is aseptic and leak-free, while at the same time being exceedingly simple.

The separate flow valve means of the present invention regulating the flow of fluid from the container by way of the third passage allows the device of the present invention to remain operably connected with the container of bulk solution between withdrawal of the various aliquots. The valve is simply closed after a particular aliquot has been withdrawn and reopened when a further aliquot is required.

The syringe disclosed as a part of the present invention enables the operator to positively and easily withdraw the desired volume of solution from the container, at the same time causing air to be drawn through the body means of the present invention to the interior of the container.

BRIEF DESCRIPTION OF THE DRAWINGS

The above and other objects of the present invention may be more fully understood from the following detailed description taken together with the accompanying drawings wherein similar reference characters refer to similar elements throughout and in which:

FIG. 1 is a perspective view of a transfer system constructed in accordance with the present invention;

FIG. 2 is a perspective view of the syringe and flow valve of the embodiment shown in FIG. 1, illustrating the withdrawal of fluid by the syringe;

FIG. 3 illustrates the structure of FIG. 2 during the ejection of fluid from the syringe;

FIG. 4 is a fragmentary vertical sectional view of the system shown in FIG. 1 taken along the line 4—4 of FIG. 1 and illustrating the open condition of the valve element therein; and FIG. 5 illustrates the structure of FIG. 4 with the valve element in the closed condition.

DESCRIPTION OF THE PREFERRED EMBODIMENTS

Referring now to the drawings there is illustrated, in FIGS. 1, 2, 3, 4 and 5 thereof, a preferred embodiment of the present invention, generally designated 10. The embodiment 10 generally comprises a container 12, a body 14, a flow valve 16, and a syringe 18.

The container 12 is shown as an intravenous bottle 20 having an open end 22 closed by a stopper 24 which is held in place by a metallic collar 26. The stopper 24 is initially imperforate and serves to maintain a sterile solution 28 within the bottle 20. The container 12 may be suspended for use in an upside down condition by a resilient bale 30 having an annular member 32 frictionally retained about the exterior of the container 12 and a bale strap 34 attached thereto for engagement with a fixed member (not shown) able to support the container 12.

The body 14 comprises a generally cylindrical portion 36 having a spike 38 extending axially therefrom and a radially outwardly directed outlet 40. In the assembled condition of the embodiment 10, the spike 38 projects upwardly through the stopper 24 to the interior of the container 12. The generally cylindrical portion 36 is thus positioned directly outside the open end 22 of the bottle 20.

The internal structure of the body 14 is most clearly seen in FIGS. 4 and 5. The body 14 may be formed of three interfitting disc elements 42, 44 and 46. The element 42 carries the axial spike 38 and the radial outlet 40 discussed above. The spike 38 is provided with a pair of parallel fluid passages 48 and 50 extending downwardly through the spike from openings 52 and 54, respectively, adjacent the outer end thereof. The passage 48 terminates in an opening 56 at the lower surface of the element 42 while the passage 50 turns radially outwardly within the element 42 and terminates in the outlet 40. The outlet 40 is a generally cylindrical projection from the surface of the element 42 and may be provided with a series of external annular ridges 58 for sealing against the bore of a piece of tubing forced over the outlet 40.

A downwardly tapered chamber 60 is provided within the body 14 essentially at the location of the element 44. The chamber 58 comprises an inverted conical cavity 62 having a generally cylindrical cavity 64 depending from its apex. The chamber 60 is located directly beneath the opening 56 of the element 42 and is bounded at the top by the lower surface of that element. The chamber 60 contains a valve element 66 which is also shaped as an inverted cone having a cylindrical portion depending from its apex. The valve element 66 is somewhat smaller than the chamber 60, enabling it to move freely in a vertical direction between the conditions of FIGS. 4 and 5. The lower surface of the element 42 adjacent the opening 56 is provided with a plurality of relatively small projections 68 which space the valve element 66 from the lower surface of the element 42 in the condition of FIG. 4.

The valve element 66 is actuated between its two conditions by changes in the pressure differential vertically across the chamber 60. The valve element 66 is in the condition of FIG. 5 when the pressure within the passage 48 is greater than the pressure in the cylindrical cavity 64 of the chamber 60. The conical portion of the valve element 66 then seals against the surface of the conical cavity 62 to prevent the downward passage of air or other fluid through the chamber 60. The pressure differential across the chamber 60 and the weight of the element 66 cause a downward sealing force to be exerted on the conical cavity 62 by the element 66. As the pressure within the passage 48 decreases, however, a point is reached at which the pressure within the cylindrical cavity 64 is greater than that within the passage 48 by an amount at least great enough to overcome the downward gravitational force on the valve element 66. At this point, the valve element 66 is actuated to the condition of FIG. 4 in which it is open to the upward passage of air through the chamber 60. The projections 68 space the valve element 66 a sufficient distance from the upper end of the chamber in this condition to enable air to flow freely about the valve element 66 to the passage 48. The valve element 66 is extremely responsive to changes in the pressure differential vertically across the chamber 60 due to the light weight of the valve element 66 and the relatively high surface area thereof. This is particularly true regarding downward movement of the element 66 due to the large circular upper surface of the element 66, however, it is also true to a substantial degree regarding upward movement of the element. The upward movement of the element 66 is thus not hindered appreciably by the weight of that element, but the element readily moves downwardly to the condition of FIG. 5 when the pressure within the cavity 64 becomes even slightly greater than the pressure within the passage 48.

A filtering membrane 70 may be sandwiched between a downwardly extending annular portion 72 of the element 44 and the periphery of a recess 74 in the upper surface of the disc element 46. A manifold 76 is thus formed between the elements 44 and 46 for the passage of air upwardly through a plurality of vertical openings 78, through the filtering membranes 70 and into the cylindrical cavity 64 of the chamber 60. The filtering membrane 70 may be a standard millipore filter.

The body 14 may be constructed of a suitable plastic or other material compatible with the solution being transferred, and the elements 42, 44 and 46 may be glued or otherwise bonded to each other in a sealing relationship, such that the chamber 60 is open only at the opening 56 and the bottom of the conical cavity 62, and the manifold 76 is open to the atmosphere only through the openings 78.

The flow valve 16 is a two-way stop cock having three fluid inlets 80, 82 and 84. The inlet 80 communicates with the outlet 40 through a length of flexible tubing 86 which engages the sealing ridges 58. The stop cock 16 is actuable between two conditions by rotation of the knob 88, as indicated in FIGS. 1, 2 and 3. In the condition of FIG. 1, the inlet 80 is sealed off while communication is provided between the inlets 82 and 84. In the condition of FIG. 2, fluid communication is provided between the inlet 80 and the inlet 82. The inlet 84 is then closed.

The syringe 18 is provided with an outlet 90 having a luer taper engageable in a sealing force fit relationship with the differently tapered bore of the inlet 82. The syringe 18 can thus be connected and disconnected with the inlet 82 of the stop cock 16. The syringe 18 is provided near the upper end of its body 92 with a pair of axially spaced flanges 94, and at the upper end of its plunger stem 96 with a thumb ring 98. The syringe 18 may thus be easily manipulated by an operator inserting his thumb in the ring 98 and the first two fingers of the same hand on either side of the body 92 between the flanges 94. The thumb ring 98 and the flanges 94 enable the operator to actuate the plunger stem 96 in either axial direction with a single hand.

In use, the system described above must first be assembled from its various components. The stopper 24 of the container 12 is initially imperforate, maintaining the sterility of the contents of the container 12 before they are needed. The body 16, tubing 86 and stop cock 16 may be packaged together in a preassembled condition. The syringe 18 may be included in the same package or packaged separately. Each of these components is designed to be disposable, eliminating the need for resterilization and greatly reducing the chances of contamination of the solution being transferred. The body 14 and the container 12 are connected by manually forcing the spike 38 of the body 14 through the stopper 24. The passages 48 and 50 are thus placed in communication with the interior of the container 12 through the openings 52 and 54. This operation is typically performed in a hospital pharmacy early in the day for transfer and administration of aliquots of the solution 28 over the course of the day. The container 12 may then be hung in an upside down condition with the bale 30 to facilitate transfer of the entire contents thereof. At this time, the stopcock 16 is in the condition illustrated in FIG. 1, wherein the inlet 80 is sealed off to prevent flow of the solution from the container.

When it is desired to remove an aliquot of solution from the container 12, the syringe 18 is connected to the inlet 82 of the stopcock 16 and the knob 88 of the stopcock is rotated counterclockwise to the condition of FIG. 2. The desired volume of the solution 28 may then be withdrawn by movement of the plunger stem 96 in the direction indicated in FIG. 2. This causes the solution 28 to be drawn through the passage 50 of the body 14, through the tubing 86 and into the syringe 18. At the same time, the pressure within the container 12 is reduced by the removal of liquid therefrom. The pressure within the passage 48 at the opening 56 directly above the chamber 60 is thus reduced to a point below the atmospheric pressure within the cylindrical cavity 64. The greater pressure in the cylindrical cavity 64 thus acts to raise the valve element 66 upwardly from the surface of the conical cavity 62 to the condition of FIG. 4, opening the valve formed thereby and allowing air to pass upwardly through the chamber 60 to the interior of the container 12. The projections 68 on the lower surface of the element 42 serve to space the valve element 66 from the element 42 in this condition to provide the optimum path for air through the chamber 60. The air does not impair the sterility of the solution 28 since it has been previously drawn through the filtering membrane 70 for removal of any contaminating particles. Upon withdrawal of the desired volume of the solution 28 by the syringe 18, the stopcock inlet 80 may be sealed off by clockwise rotation of the knob 88, as shown in FIG. 3. The flow of fluid through the passage 50 from the container 12 is thus halted and the volume of liquid within the container becomes constant. The pressure within the container 12 then becomes equalized to a large extent with the atmospheric pressure, causing the pressure within the passage 48 at the opening 56 to become substantially equal to the atmospheric pressure within the cylindrical cavity 64. The upward force on the valve element 66 caused by the pressure differential across the chamber 60 is thus removed, causing the valve element 66 to fall from the open condition of FIG. 4 to the closed condition of FIG. 5. The flow of additional air through the chamber 60 is prevented, once again sealing the container 12 from the atmosphere. No amount of fluid pressure within the passage 48 can cause the downward leakage of fluid through the chamber 60 because any increase in pressure only forces the valve element more securely against the valve seat formed by the conical cavity 66, preventing such fluid flow. The present invention thus allows the partial vacuum formed within the container 12 from the withdrawal of fluid therefrom to be relieved automatically by the body 14, but entirely eliminates the possibility of fluid leakage from the container. At the same time, the contents of the container 12 is maintained in the desired sterile condition by the filtration of the air allowed to enter the container.

Once the desired volume of solution has been drawn into the syringe 18 and the stopcock has been placed in the condition of FIG. 3, the contents of the syringe can be expelled from the inlet 84 of the stopcock 16 by depression of plunger stem 96. A piece of sterile tubing or an injection needle can be connected to the inlet 84 to carry the solution to a partially filled IV bottle or other container. Alternatively, the syringe 18 can be removed from the stopcock 16 and fitted with a standard needle having a luer fitment for direct injection into an IV container.

The procedure outlined above for withdrawal of a single aliquot of solution from the container 12 may be repeated over a period of time until the contents of the container 12 have been expended. The entire embodiment 10 may then be discarded and a new one assembled from a set of sterile components including a new container 12. For this purpose, the various components of the present invention have been designed to be manufactured easily and inexpensively from any of a variety of suitable plastic materials. The valve element 66 is preferably made of a resilient rubber-like material to form an effective seal with the surface of the conical cavity 62.

It will be understood that the solution 28 may be drawn from the container 12 by a gravity feed system as well as by the syringe 18 discussed above. In such a system, the stopcock 16 would simply be a two-inlet stopcock having an open and closed condition between the inlets.

It will be further understood that the vertical orientation of the valve element 66 and the chamber 60 described herein is illustrative only, and the poppet valve formed thereby will function in the desired way in any orientation. This is true because the element 66 is relatively light and is very responsive to air pressure within the chamber 60. The gravitational force on the element 66 is thus negligible in comparison to the other forces acting thereon and does not interfere with the intended operation of the device.

From the above, it can be seen that there has been provided an improved system for the aseptic transfer of aliquots of a sterile solution from a bulk container.

The appended claims are intended to cover all variations and adaptations falling within the true scope and spirt of the present invention.

I claim:

1. A transfer device for the withdrawal of aliquots from a container of bulk solution comprising:
    body means having:
      first walls defining a tapered chamber;
      second walls defining a first passage venting the smaller end of said chamber to the surrounding air;
      third walls defining a second passage communicating at one end with the larger end of said chamber; and
      fourth walls defining a third passage having one end for withdrawal of fluid therefrom, said third passage being free of communication with said first and second passages and said chamber within said body means;
    a tapered valve element received within said chamber for movement between first and second conditions in response to changes in the pressure differential between the first and second passages, said first condition providing a fluid seal between the first and second passages by engagement of said valve element with said first walls of the chamber for pressures within the second passage greater than that within the first passage, and said second condition providing a fluid path from the first passage to the second passage for pressures within the second passage less than that within the first passage; and
    means for placing the other ends of said second and third passages in communication with the interior of the container of bulk solution;
    whereby a path is provided for air to be drawn into the container through the first and second passages when aliquots are withdrawn from the container through the third passage, but fluid is not able to escape from the container through the first and second passages.

2. The transfer device recited in claim 1 which includes a filter element within said first passage for removing impurities from air passing therethrough.

3. The transfer device recited in claim 2 wherein said filter element is a millipore filter extending across said first passage at an enlarged portion thereof.

4. The transfer device recited in claim 1 wherein said valve element is resilient.

5. The transfer device recited in claim 1 wherein said tapered chamber comprises a conical cavity having a coaxial cylindrical cavity depending from its apex, said first passage communicating with said chamber through said cylindrical cavity.

6. The transfer device recited in claim 4 wherein said valve element comprises a conical member having a coaxial cylindrical portion depending from its apex, the valve element being somewhat smaller than the chamber for movement therein between said first and second conditions.

7. The transfer device recited in claim 1 for use with a container of bulk solution closed by an imperforate stopper, wherein said means for placing the other ends of said second and third passages in communication with the interior of the container of bulk solution comprises stopper piercing means projecting from said body means and having a sharpened outer end, said stopper piercing means having a pair of passages extending from the other ends of said second and third passages, respectively, to corresponding openings adjacent said sharpened outer end.

8. A system for the dispensation of aliquots of a bulk solution, comprising:
    a container of bulk solution; and
    a transfer device comprising;
      body means having:
        first walls defining a tapered chamber;

second walls defining a first passage venting the smaller end of said chamber to the surrounding air;

third walls defining a second passage communicating at one end with the larger end of said chamber; and fourth walls defining a third passage having one end for withdrawal of fluid therefrom, said third passage being free of communication with said first and second passages and said chamber within said body means;

a tapered valve element received within said chamber for movement between first and second conditions in response to changes in the pressure differential between the first and second passages, said first condition providing a fluid seal between the first and second passages by engagement of said valve element with said first walls of the chamber for pressures within the second passage greater than that within the first passage, and said second condition providing a fluid path from the first passage to the second passage for pressures within the second passage less than that within the first passage; and means for placing the other ends of said second and third passages in communication with the interior of the container of bulk solution;

whereby a path is provided for air to be drawn into the container through the first and second passages when aliquots are withdrawn from the container through the third passage, but fluid is not able to escape from the container through the first and second passages.

9. A system for the dispensation of aliquots of a bulk solution, comprising:

a container of bulk solution; and a transfer device comprising:

body means having:

first walls defining a tapered chamber;

second walls defining a first passage venting the smaller end of said chamber to the surrounding air;

third walls defining a second passage communicating at one end with the larger end of said chamber; and fourth walls defining a third passage having one end for withdrawal of fluid therefrom, said third passage being free of communication with said first and second passages and said chamber within said body means;

a tapered valve element received within said chamber for movement between first and second conditions in response to changes in the pressure differential between the first and second passages, said first condition providing a fluid seal between the first and second passages by engagement of said valve element with said first walls of the chamber for pressures within the second passage greater than that within the first passage, and said second condition providing a fluid path from the first passage to the second passage for pressures within the second passage less than that within the first passage; and means for placing the other ends of said second and third passages in communication with the interior of the container of bulk solution; and flow valve means having first and second ports, said first port communicating with said one end of the third passage and said flow valve means operable between a first condition providing a fluid path between the first and second ports and a second condition providing a fluid seal between the first and second ports;

whereby withdrawal of fluid from the second port for the valve means in said first condition causes fluid to be drawn from the container through the third passage of the body means and provides a path for air to be simultaneously drawn into the container through the first and second passages of the body means, but fluid is in no event able to escape from the container through the first and second passages.

10. The system recited in claim 9 which includes a syringe connectible to the second port of the valve means for withdrawal of fluid therefrom.

11. The system recited in claim 10 wherein said flow valve means includes a third port which is out of communication with the first and second ports within the valve means for the valve means in the first condition and which communicates with the second port for the valve means in the second condition, whereby an aliquot of fluid drawn into said syringe from the container of bulk solution can be expelled from the syringe through said third port for the valve means in the second condition.

12. The system recited in claim 11 wherein the flow valve means comprises a two-position stopcock.

13. The transfer device recited in claim 9 which includes a filter element within said first passage for removing impurities from air passing therethrough.

14. The transfer device recited in claim 9 wherein said valve element is resilient.

15. The transfer device recited in claim 9 wherein said tapered chamber comprises a conical cavity having a coaxial cylindrical cavity depending from its apex, said first passage communicating with said chamber through said cylindrical cavity.

16. The transfer device recited in claim 15 wherein said valve element comprises a conical member having a coaxial cylindrical portion depending from its apex, the valve element being somewhat smaller than the chamber for movement therein between said first and second conditions.

17. The transfer device recited in claim 9 for use with a container of bulk solution closed by an imperforate stopper, wherein said means for placing the other ends of said second and third passages in communication with the interior of the container of bulk solution comprises stopper piercing means projecting from said body means and having a sharpened outer end, said stopper piercing means having a pair of passages extending from the other ends of said second and third passages, respectively, to corresponding openings adjacent said sharpened outer ends.

* * * * *